United States Patent [19]

Mühlegger et al.

[11] 4,148,994
[45] Apr. 10, 1979

[54] CRYSTALLINE METAL SALTS OF β-NICOTINAMIDE-ADENINE-DINUCLEOTIDE

[75] Inventors: Klaus Mühlegger, Weilheim; Günter Weimann; Michael Nelboeck-Hochstetter, both of Tutzing, all of Fed. Rep. of Germany

[73] Assignee: Boehringer Mannheim GmbH, Mannheim-Waldhof, Fed. Rep. of Germany

[21] Appl. No.: 754,879

[22] Filed: Dec. 27, 1976

[30] Foreign Application Priority Data

Aug. 20, 1976 [DE] Fed. Rep. of Germany ....... 2637598

[51] Int. Cl.$^2$ ..................... C07H 17/00; A61K 31/70
[52] U.S. Cl. ........................................ 536/28; 536/27; 424/180
[58] Field of Search ............................. 536/26, 27, 28

[56] References Cited

U.S. PATENT DOCUMENTS

| | | | |
|---|---|---|---|
| 3,429,868 | 2/1969 | Kominato et al. | 536/28 |
| 3,700,654 | 10/1972 | Brusca et al. | 536/27 |
| 3,749,709 | 7/1973 | Nelboeck-Hochstetter et al. | 536/27 |
| 3,787,392 | 1/1974 | Bergmeyer et al. | 536/27 |

*Primary Examiner*—Johnnie R. Brown
*Assistant Examiner*—Blondel Hazel
*Attorney, Agent, or Firm*—Sprung, Felfe, Horn, Lynch & Kramer

[57] ABSTRACT

Crystalline salts of β-nicotinamide-adenine-dinucleotide (β-NAD), particularly alkali metal salts thereof are prepared in good yield and high quality to provide an analytically useful β-NAD form.

1 Claim, No Drawings

CRYSTALLINE METAL SALTS OF β-NICOTINAMIDE-ADENINE-DINUCLEOTIDE

The present invention relates to β-nicotinamide-adenine-dinucleotide (β-NAD), particularly to crystalline metal salts of β-nicotinamide-adenine-dinucleotide, and with the preparation thereof.

β-NAD occurs as the coenzyme of numerous dehydrogenases in all living organisms and plays a key role in biochemical redox processes. The compound was discovered in 1904 by Harden and Young in their investigations into alcoholic fermentation and its chemical constitution was elucidated by Warburg and Christian in 1934. Recently, β-NAD has achieved considerable importance, especially as a measurement parameter in enzymatic analysis in the determination of enzyme activities and substrate concentrations for clinical diagnosis. Consequently, the extent of the production of NAD has considerably increased worldwide.

However, great disturbances and erroneous results in enzymatic analyses with NAD have been observed when the NAD used is contaminated (see, for example, Dalziel, J. Biol. Chem., 238, 1538/1963) since even fragments of the NAD molecule are themselves strongly competitive inhibitors of the co-enzyme. Therefore, attempts have already been made to prepare especially pure NAD by crystallization. Wallenfels and Christian first succeeded in crystallizing NAD in the form of its quinine salt (see K. Wallenfels and W. Christian in S. P. Colowick and N. O. Kaplan, Methods in Enzymology, Vol. 3, pub. Academic Press, New York, 1957, page 882). Subsequently, (see A. D. Winer, J. Biol. Chem., 239, P.C. 3598/1964) the crystallization of NAD in the form of the free acid was reported.

However, none of these processes for the crystallization of β-NAD have achieved practical importance since, because of poorly standardisable parameters, they are not reproducible, are laborious to carry out, give rise to very high losses with regard to yield and also are not satisfactory with regard to the quality of the product obtained.

In the case of all the processes at present used for the production of NAD, in the final stage, a solution is obtained which is brought into solid form by processes such as, for example, precipitation with organic solvents, spray drying and/or freeze drying. The NAD obtained according to these processes is amorphous, very hygroscopic and deliquesces in the air. The instability of the amorphous NAD requires special and usually very expensive precautions (exclusion of air, use of protective gas and the like) during storage, despatch and working up. In spite of special precautions, however, variations in the quality of the product cannot be avoided, with the result that considerable difficulties often occur.

The present invention substantially avoids these disadvantages and provides crystallized β-NAD derivatives which are stable under normal conditions and which can be prepared simply, reproducibly and in good yields.

The present invention provides crystalline metal salts, preferably alkali metal salts, of β-nicotinamide-adenine-dinucleotide.

A particularly preferred crystalline salt according to the present invention is the orthorhombic monolithium salt of β-nicotinamide-adenine-dinucleotide dihydrate with the space group $P2_1 2_1 2_1$, the cell dimensions $a = 10.073 \pm 0.003$ Å, $b = 15.839 \pm 0.004$ Å, $c = 17.821 \pm 0.004$ Å and the angles $\alpha = \beta = \gamma = 90°$.

The present invention also provides a process for the preparation of the metal slats of β-NAD, wherein β-nicotinamide-adenine-dinucleotide in the form of the free acid or of a salt thereof is converted in known manner into a dilute aqueous solution of a metal salt of β-nicotinamide-adenine-dinucleotide, the pH value is adjusted to from 3 to 7, preferably from 3.7 to 4.0, the solution is mixed at a temperature of from 10° to 50° C. and preferably at ambient temperature, with a water-miscible organic solvent until the commencement of turbidity and crystallization is carried out at a temperature of from 4° to 30° C.

The water-miscible organic solvent used according to the present invention can, in principle, be any solvent which has this property. However, there are preferably used lower alcohols, ketones, nitriles and cyclic ethers, especially methanol, ethanol, n-propanol, isopropanol, acetone, acetonitrile or dioxan.

If, in the preparation of the metal salt of β-NAD, there are not used, as starting materials, appropriately precipitated, spray-dried and/or lyophilised amorphous metal salts of β-NAD, the NAD in the form of the free acid or of one of its salts can easily be converted in the usual manner into the β-NAD metal salt. NAD in the form of the free acid can be converted into the metal salt, for example, by passage through an ion exchanger loaded with the appropriate metallic ions (for example, an ion exchanger of the Dowex 50 or IR 20 type) or by careful adjustment of the appropriate pH value with a dilute aqueous solution of a metal hydroxide. NAD salts can also be converted into the desired β-NAD salts by treatment with, for example, an ion exchanger loaded with the desired metal ions.

For the preparation of the especially preferred orthorhombic monolithium salt of β-NAD dihydrate, it is preferred to start from the amorphous monolithium salt of β-NAD or from β-NAD in the form of the free acid. The free acid can be converted into the lithium salt by passage through an ion exchanger loaded with lithium ions or by careful adjustment of th pH value with a dilute aqueous solution of lithium hydroxide.

The metal salts according to the present invention do not have the disadvantages of the previously isolated, known NAD derivatives; they are non-hygroscopic, flowable, storage-stable and, in chemical and enzymatic analysis, give a content of 100% ($\pm 0.2\%$), referred to the β-NAD. The salts are white and completely odourless. The usual main contaminants of commercially available β-NAD, especially α-NAD and ADP-ribose, are, at most, only detectable in the products according to the present invention in traces.

The process according to the present invention has the advantage that the yields of the metal salts of β-NAD are almost quantitative. The products prepared by this process give, in the enzyme kinetics, in comparison with the best commercially-available preparations, a value which is 10 to 20% higher. Furthermore, the process according to the present invention is technically less laborious than the known methods for the isolation of solid NAD derivatives and thus is more economic.

Apart from the above-described manner, the monolithium salt of β-NAD dihydrate can also be obtained in crystalline form from pure water when an aqueous solution of NAD is left to stand at ambient temperature at a concentration of from 100 to 1000 mg./ml., preferably of about 500 mg./ml., for some time at a pH value of about 3.7. In principle, the recrystallization can be carried out by warming to an elevated temperature (up to about 60° C.) and subsequently slowly cooling to ambient temperature, although the yields of the pure product obtained according to this process are reduced due to the sensitivity of the substance.

The following Examples are given for the purpose of illustrating the present invention:

EXAMPLE 1

1 g. β-NAD lithium salt (prepared by the passage of a solution of the free acid through Dowex 50 in the lithium form and subsequent lyophilization) is dissolved in 2 ml. of water, mixed dropwise at ambient temperature, while stirring, with 1.2 ml. acetone until the turbidity still just disappears, whereafter the solution is left to crystallize at 20° to 25° C. The product which crystallizes out is, after 30 hours, filtered off with suction, washed twice with a little acetone-water (1:2 v/v) and dried in a vacuum over phosphorus pentoxide. The yield is 900 mg. (90% of the lyophilisate used initially).

EXAMPLE 2

1 g. lyophilised β-NAD lithium salt is dissolved in 2 ml. water and mixed dropwise at ambient temperature, while stirring, with 3.6 ml. methanol until the turbidity still just disappears and then worked up in the manner described in Example 1. After drying, there are obtained 900 mg. (90% of the amount initially used) of crystalline lithium salt.

EXAMPLE 3

1 g. β-NAD in the form of the lyophilised free acid is dissolved in 0.75 ml. water and the pH adjusted to 4 by the dropwise addition of 1.3 ml. 1 N aqueous lithium hydroxide solution, 2 ml. methanol are then added thereto and the mixture left to stand for about 30 hours at 20° to 25° C. After working up in the manner described in Example 1, there are obtained 900 g. (90% of the amount initially used) of crystalline β-NAD lithium salt.

EXAMPLE 4

1 g. lyophilised β-NAD lithium salt is dissolved in 2 ml. water and mixed, in the manner described in Example 1, with 0.8 ml. isopropanol. After suction filtration, washing and drying, there are obtained 800 mg. (80% of the amount initially used) of crystalline lithium salt.

EXAMPLE 5

0.5 g. of lyophilised β-NAD lithium salt are dissolved in 1 ml. water and mixed with 0.85 ml. dioxan in the manner described in Example 1. The crystallization yield is 70% of the amount of lyophilisate initially used.

EXAMPLE 6

0.5 g. of lyophilised β-NAD lithium salt are dissolved in 1 ml. water and slowly mixed with 0.4 ml. acetonitrile in the manner described in Example 1. The crystalline lithium salt is obtained in a yield of 80%, referred to the amount of lyophilisate initially used.

EXAMPLE 7

0.5 g. of lyophilised β-NAD lithium salt are dissolved in 1 ml. water and left to stand at ambient temperature. After 5 to 6 days, the separation of crystals commences; the solution is left to stand for a further 3 to 4 days for completion of the crystallization. The yield is 40%, referred to the amount of lyophilisate used.

Analysis of the orthorhombic monolithium salt: sum formula: $C_{21}H_{26}N_7O_{14}P_2Li \cdot 2H_2O$ molecular weight: 705.4
NAD (determined enzymatically with ADH): 93.5%
water: 5.5% by weight
lithium: 1.17% by weight
m.p. 203°–203.5° C. (decomp.) (Uncorrected)
elementary analysis: found: C,35.28%; H,3.99%; N,13.59%; P,8.73%. calc.: C,35.76%; H,4.28%; N,13.90%; P,8.78%.

crystallographic data:
crystal system: orthorhombic
angles: $\alpha, \beta, \gamma$: all 90°
space group: $P2_1 2_1 2_1$
cell dimensions:
a = 10.073 ± 0.003 Å
b = 15.839 ± 0.004 Å
c = 17.821 ± 0.004 Å
crystal density: 1.65 g/cc.

The crystals consist of a formula unit in the asymmetrical unit.

It will be understood that the specification and examples are illustrative but not limitative of the present invention and that other embodiments within the spirit and scope of the invention will suggest themselves to those skilled in the art.

What is claimed is:
1. Orhtorhombic monolithium salt of beta-nicotinamide-adenine-dinucleotide hydrate with the following characteristics:
the space group $P2_1 2_1 2_1$,
the cell dimensions a = 10.073 ± 0.003 Å, b = 15.839 ± 0.004 Å, c = 17.821 ± 0.004 Å, and the angles alpha = beta = gamma = 90°.

* * * * *